(12) United States Patent
Suda et al.

(10) Patent No.: US 8,236,873 B2
(45) Date of Patent: Aug. 7, 2012

(54) METHOD OF MANUFACTURING PROTEIN ADSORPTION PREVENTING EYE LENS MATERIAL

(75) Inventors: Yukimitsu Suda, Kanagawa (JP); Kazuyuki Miyazawa, Kanagawa (JP); Kazuhiko Ishihara, Mitaka (JP)

(73) Assignee: Shiseido Co., Ltd., Tokyo (JP)

( * ) Notice: Subject to any disclaimer, the term of this patent is extended or adjusted under 35 U.S.C. 154(b) by 1130 days.

(21) Appl. No.: 10/593,544

(22) PCT Filed: May 18, 2005

(86) PCT No.: PCT/JP2005/009084
§ 371 (c)(1),
(2), (4) Date: Sep. 23, 2007

(87) PCT Pub. No.: WO2005/114306
PCT Pub. Date: Dec. 1, 2005

(65) Prior Publication Data
US 2009/0156741 A1    Jun. 18, 2009

(30) Foreign Application Priority Data

May 24, 2004 (JP) ................................ 2004-153256
May 10, 2005 (JP) ................................ 2005-136847

(51) Int. Cl.
*G02B 1/04* (2006.01)
(52) U.S. Cl. ............... 523/106; 351/160 R; 524/503; 524/599; 524/610; 524/612; 525/61; 525/326.1; 525/328.8; 525/330.3; 525/330.5; 525/340; 525/450
(58) Field of Classification Search .............. 351/160 R; 523/106; 525/61, 326.1, 328.8, 330.3, 340, 525/330.5, 450; 524/503, 599, 610, 612
See application file for complete search history.

(56) References Cited

U.S. PATENT DOCUMENTS 5,466,853 A * 11/1995 Koinuma et al. ............. 558/169
5,936,703 A * 8/1999 Miyazaki et al. ......... 351/160 R

FOREIGN PATENT DOCUMENTS

JP         09327288 A  * 12/1997

* cited by examiner

*Primary Examiner* — David W Wu
*Assistant Examiner* — Marie Reddick
(74) *Attorney, Agent, or Firm* — Townsend & Banta

(57) ABSTRACT

An eye lens material preventing protein adsorption is manufactured by reacting in a reaction medium of either water, an organic solvent, or a water/organic solvent mixture an eye lens material having OH groups with a phosphorylcholine group-containing compound of formula (1), thereby forming an acetal bond according to formula (2) which covalently bonds the phosphorylcholine group-containing compound to a surface of the eye lens material.

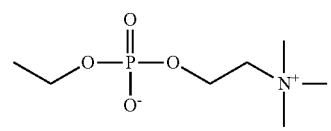

(1)

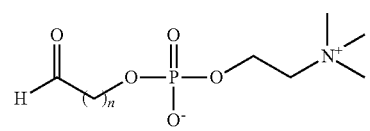

(2)

*n* denotes a natural number 1-18.

6 Claims, 1 Drawing Sheet

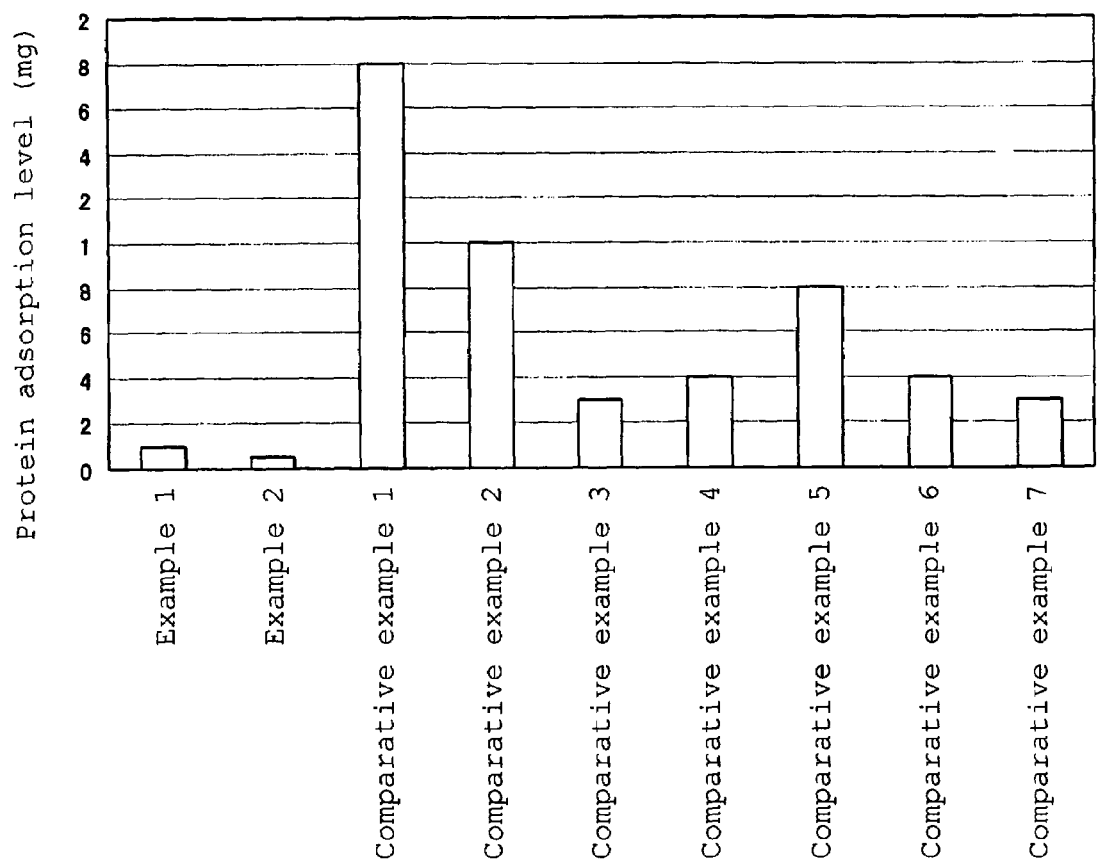

US 8,236,873 B2

METHOD OF MANUFACTURING PROTEIN ADSORPTION PREVENTING EYE LENS MATERIAL

TECHNICAL FIELD

The present invention relates to an eye lens material such as a contact lens, a method of manufacturing it, and a method of preventing protein adsorption. More specifically, it relates to a method of preventing protein stains by treating the surface of an eye lens material (particularly for contact lenses) by means of an after-treatment using a phosphorylcholine group-containing chemical compound.

BACKGROUND ART

The practice of polymerizing phosphorylcholine group-containing monomers for use as a contact lens material is a prior art (Patent Documents 1-3). For example, Patent Document 1 discloses a moist soft contact lens containing a phosphorylcholine group-containing (meth)acrylic ester as a constitutional unit; it is described as having superior moisture content, oxygen permeability, and tensile strength, as well as reduced protein adsorption and the ability to suppress stain adhesion.

As an example of an after-treatment method for contact lenses, Patent Document 4 describes polymerization of phosphorylcholine group-containing monomers on the contact lens surface to prepare a contact lens having hydrophilic surfaces and reduced protein adsorption.

In addition, Patent Document 5 describes a reduction in protein adsorption by chemically bonding a low molecular weight phosphorylcholine compound onto the contact lens surface.

That is, Example 5 of Patent Document 5 claims that the adhesion of albumin and lysozyme onto a contact lens can be suppressed by treating a 4-hydroxyethyl methacrylate-co-methacryl acid copolymer contact lens with 2-[{2-(1-imidazolecarbonyloxyethoxy)hydroxyphosphinyl}oxy]-N,N,N-trimethyletanaminiumnitroxide inner salt.

However, the method described in Patent Document 5 uses a very cumbersome method with many steps, which makes it very hard to obtain the target substance with a high yield and high purity. Also, the reaction to introduce phosphorylcholine groups onto the contact lens surface, under the conditions described in these Patent Documents, does not proceed sufficiently and results in a low introduction level, and therefore a superior protein adsorption prevention effect is not achieved.

Stains on a contact lens result from adsorption of proteins and/or lipids contained in lacrimal fluid; these stains can cause eye troubles such as allergies and infections (Non-patent Document 1). Protein stains cause a fatal problem particularly for a moist contact lens whose main ingredient is a 2-hydroxyethyl methacrylate polymer, a highly moist soft contact lens prepared by copolymerizing this ingredient with a small amount of methacrylic acid, which is an ionic monomer, and a soft contact lens whose main ingredient is a polymer of a hydrophilic monomer such as N-vinyl pyrrolidone and N,N-dimethyl acrylamide.

Patent Document 1: Japanese Patent Laid-Open H10-177152 bulletin
Patent Document 2: Japanese Patent Laid-Open 2000-111847 bulletin
Patent Document 3: Japanese Patent Laid-Open 2000-169526 bulletin
Patent Document 4: Japanese Patent Laid-Open 2001-337298 bulletin
Patent Document 5: Japanese Patent Laid-Open H5-505121 bulletin
Non-patent Document 1: "Stains on soft contact lenses and analysis thereof", Material Stage, Vol. 4, No. 1, 2004

DISCLOSURE OF INVENTION

Problem that the Present Invention Aims to Solve

The present invention provides a contact lens that prevents protein stains by suppressing protein adsorption on the contact lens by means of an after-treatment in which phosphorylcholine groups are covalently bonded onto the contact lens surface via a chemical compound having a terminal amino group.

That is, the present invention does not prepare a protein adsorption prevention contact lens by polymerizing monomers having phosphorylcholine groups, as in the methods described in Patent Documents 1-3 above; its object is to give contact lenses a superior protein adsorption prevention function by means of an after-treatment.

Also, the present invention does not introduce phosphorylcholine groups by polymerizing phosphorylcholine-containing monomers onto the contact lens surface to coat it with a polymer different from the contact lens itself, as in a method described in Patent Document 4; it uses direct covalent bonding of phosphorylcholine groups, rather than polymer coating, and thus aims to achieve a superior protein adsorption prevention effect without changing the original characteristics of the contact lens with polymer coating.

Furthermore, the present invention aims to achieve a superior protein adsorption prevention effect by introducing a sufficient amount of phosphorylcholine, as opposed to the method described in Reference 5, which is shown to be incapable of introducing a sufficient amount of phosphorylcholine groups onto the contact lens surface when an attempt to duplicate this method is actually made.

That is, the essential difference between the present invention and the method shown in Patent Document 5 is a difference in the introduction efficiency of the phosphorylcholine group onto the contact lens surface; this difference led to the superior effect of more efficiently suppressing protein adsorption.

An advantage of the present invention lies in the fact that phosphorylcholine groups can be stably introduced onto a contact lens material having hydroxyl groups on the surface by means of acetal bonding in any solvent: water or organic solvents.

Means to Solve the Problem

That is, the present invention provides a method of manufacturing an eye lens material having a process in which a phosphorylcholine group-containing chemical compound represented by the following formula (1) is reacted and covalently bonded onto the surface of an eye lens material wherein the chemical compound represented by the following formula (2) is reacted and covalently bonded through acetal bonding to the eye lens material having OH groups in water, an organic solvent, or a water/organic solvent mixture.

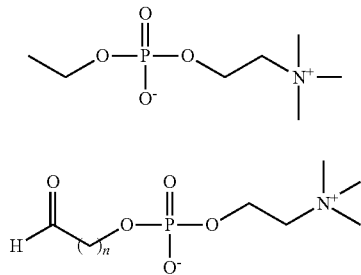

n denotes a natural number 1-18.

Also, the present invention provides the aforementioned method of manufacturing an eye lens material wherein constituent monomers of said eye lens material include monomers containing a hydroxyl group.

Furthermore, the present invention provides the aforementioned method of manufacturing an eye lens material wherein constituent monomers of said eye lens material include 2-hydroxyethyl methacrylate.

Furthermore, the present invention provides the aforementioned method of manufacturing an eye lens material wherein constituent ingredients of said eye lens material include polyvinyl alcohol.

That is, the present invention provides a method of manufacturing an eye lens material having a process in which a phosphorylcholine group-containing chemical compound represented by the following formula (1) is reacted and covalently bonded onto the surface of an eye lens material wherein OH groups are introduced to the surface of the eye lens material by means of a plasma treatment and then the chemical compound represented by the following formula (2) is reacted and covalently bonded through acetal bonding in water, an organic solvent, or a water/organic solvent mixture.

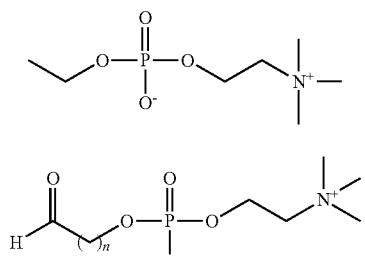

wherein n denotes a natural number 1-18.

That is, the present invention provides an eye lens material characteristically obtained with a method of manufacturing an eye lens material having a process in which a phosphorylcholine group-containing chemical compound represented by the following formula (1) is reacted and covalently bonded onto the surface of an eye lens material wherein the chemical compound represented by the following formula (2) is reacted and covalently bonded through acetal bonding to the eye lens material having OH groups in water, an organic solvent, or a water/organic solvent mixture.

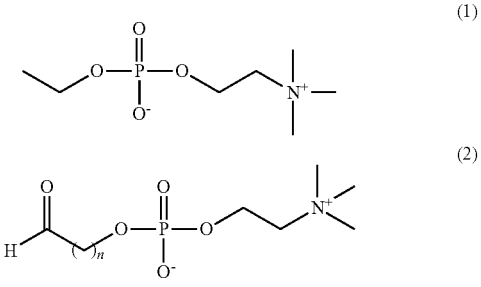

wherein n denotes a natural number 1-18.

That is, the present invention provides an eye lens material characteristically obtained with a method of manufacturing an eye lens material having a process in which a phosphorylcholine group-containing chemical compound represented by the following formula (1) is reacted and covalently bonded onto the surface of an eye lens material wherein OH groups are introduced to the surface of the eye lens material by means of a plasma treatment and then the chemical compound represented by the following formula (2) is reacted and covalently bonded through acetal bonding in water, an organic solvent, or a water/organic solvent mixture.

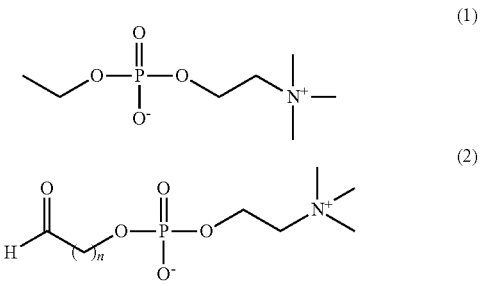

wherein n denotes a natural number 1-18.

Also, the present invention provides a protein adsorption prevention method wherein protein adsorption on an eye lens material is prevented by means of an after-treatment in which the chemical compound represented by the following formula (2) is reacted and covalently bonded through acetal bonding to the eye lens material having OH groups in water, an organic solvent, or a water/organic solvent mixture.

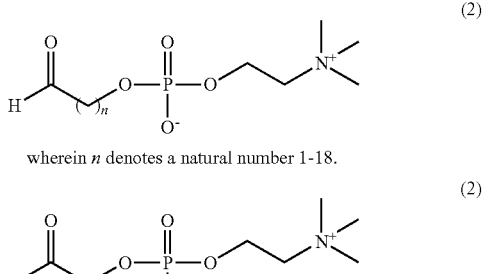

n denotes a natural number 1-18.

Effects of the Invention

The manufacturing method of the present invention uses a simple after-treatment method to covalently bond any amount of phosphorylcholine groups onto the eye lens material surface by means of acetal bonding.

An important advantage lies in the fact that the chemical compound of formula (2) can be introduced by means of acetal bonding in either water or an organic solvent. That is, as opposed to ester bonding by esterification, this method has an advantage in that the after-treatment of an eye lens material having hydroxyl groups can be carried out in water.

Since there is no condition for the esterification reaction to proceed in water, acetalization is a superior technique that can introduce phosphorylcholine groups in water or a water-containing organic solvent.

That is, when the manufacturing method of the present invention is used, the after-treatment does not have to be carried out under strictly water free conditions. Also, when the after-treatment is done in water, there is another advantage in that the eye lens material will not be altered by an organic solvent.

The eye lens material of the present invention is a contact lens onto whose surface phosphorylcholine groups are covalently bonded by means of acetal bonding and therefore it effectively suppresses protein adsorption on the contact lens and achieves a superior stain prevention effect. It can also improve moisture retention and the sensation of wearing the contact lens.

Also, since the protein adsorption prevention function can be added by means of an after-treatment, the present invention can be easily used on existing contact lenses.

Since polymer coating is not used as the method to introduce the phosphorylcholine groups, durability is superior and the original characteristics of the contact lens are essentially not degraded.

The contact lens obtained by the present invention is a contact lens that gives a superior sensation when it is worn. Therefore it can be preferably used in situations where wearing contact lenses tends to feel like a foreign body is touching the eye due to reasons such as poor flexibility of the material.

In particular, the reaction between OH group on the contact lens surface and the chemical compound of formula (2) has a very high yield and allows easy control of the amount to be introduced. Therefore, the present invention has the superior effect of very efficiently introducing the phosphorylcholine group of formula (1) onto the contact lens surface.

BRIEF DESCRIPTION OF DRAWINGS

FIG. 1 is a graph showing protein adsorption on the contact lenses of Examples and Comparative examples.

BEST MODE FOR CARRYING OUT THE INVENTION

The present invention is described in detail below.
"A Method of Preparing the Phosphorylcholine Group-Containing Chemical Compound of Formula (2)"

This chemical compound can be synthesized by means of total synthesis. However, the synthesis conditions are cumbersome, a strict moisture-free condition is required, and therefore the manufacturing cost is high. On the other hand, phosphorylcholine can be extracted as lecithin, which is a constituent component of cell membranes; by removing the fatty acid portion by means of hydrolysis, phosphorylcholine can be easily obtained at low cost in the form of 1-α-glycerophosphorylcholine. The inventors discovered that a phosphorylcholine group-containing chemical compound having an aldehyde group can easily be obtained by means of oxidative cleavage of the diol portion of this 1-α-glycerophosphorylcholine. The most representative synthesis method oxidizes 1-α-glycerophosphorylcholine by using sodium periodate in water to obtain the target aldehyde derivative; the oxidant and solvent are not limited to these chemical compounds.
"A Method of Manufacturing the Chemical Compound of Formula (2) by Means of Oxidative Cleavage of 1-α-glycerophosphorylcholine"

1-α-glycerophosphorylcholine can be oxidatively cleaved by periodate to obtain the chemical compound of formula (2).
"An Eye Lens Material"

The eye lens material in the present invention refers to a molded piece of a material that is worn in the eye. It mainly refers to a contact lens. A contact lens of any material can be used. The contact lens of the present invention can be prepared from a contact lens comprising a polymer such as methacrylic acid (MAA), acrylic acid (AA), 2-hydroxyethyl methacrylate (HEMA), N-vinylpyrrolidone, N,N-dimethylacrylamide, vinyl acetate, methyl methacrylate, trifluoroethyl methacrylate, cellulose acetate butyrate, fluoro silicone, hexafluoroisopropyl methacrylate, perfluoroalkyl methacrylate, siloxanyl methacrylate, siloxanyl styrene, ethylene glycol dimethacrylate, allyl methacrylate (AMA), and silicone macromers, as well as a copolymer of two or more types of monomers, or a contact lens whose constituent ingredients include polyvinyl alcohol and/or polysiloxane.

The present invention is independent of the type of monomer, and it can be used for both hard contact lenses and soft contact lenses.

A soft contact lens that uses 2-hydroxyethyl methacrylate as the main constituent ingredient and an ionic soft contact lens prepared by copolymerizing it with methacrylic acid are representative soft contact lenses; these contact lenses are susceptible to protein adsorption. Therefore, they are preferably treated with the method of the present invention.

Also, a contact lens whose constituent ingredients include vinyl alcohol or poly-N-vinyl pyrrolidone is also treated preferably with the method of the present invention.

Furthermore, hard contact lenses having methyl (meth) acrylate as a main ingredient of constituent monomers and hard contact lenses for extended wear, and/or with oxygen permeability, to which proteins tend to be adsorbed, are also preferably treated with the method of the present invention.

A contact lens that contains 2-hydroxyethyl methacrylate and/or polyvinyl alcohol polymer as a functional group to which the phosphorylcholine group-containing chemical compound of the aforementioned formula (2) can covalently bond is preferable because it has hydroxyl groups.

However, even if these functional groups are not present, hydroxyl groups can be introduced by means of a plasma treatment. For example, hydroxyl groups can be introduced onto a contact lens comprising N-vinyl pyrrolidone polymer to prepare the contact lens of the present invention. That is, hydroxyl groups are introduced onto the contact lens surface by using low temperature plasma in an oxygen gas atmosphere or oxygen/hydrogen gas atmosphere. Specifically, the contact lens is put into a plasma reactor vessel and, after a vacuum pump is used to form a vacuum in the reactor vessel, oxygen gas or oxygen/hydrogen gas is introduced. Hydroxyl groups can then be introduced onto the contact lens surface by means of glow discharge.

The phosphorylcholine group-containing chemical compound of formula (2), through acetal bonding, forms a strong covalent bond with the hydroxyl group on the contact lens surface.

The present invention means that phosphorylcholine groups are introduced directly onto the contact lens surface by means of covalent bonding through acetal bonding. Therefore, the present invention does not include cases in which the chemical compound of formula (2) is bonded to a contact lens whose surface is coated with a polymer having OH groups.
"A Method of Manufacturing a Protein Adsorption Prevention Contact Lens"

Since the essence of the present invention lies in the fact that the phosphorylcholine group-containing chemical compound represented by formula (2) is covalently bonded onto the contact lens surface by means of direct acetal bonding, a method of manufacturing it is not limited, i.e. acetal bonding can be done with any method. However, as explained above, it does not include embodiments in which the contact lens surface is coated with a polymer having OH groups and then the chemical compound of formula (2) is acetal-bonded. This is because the coating polymer can peel off and/or there may be an influence from the coating polymer.

Specifically, using a conventional method in an organic solvent, the chemical compound of formula (2) is covalently bonded to the hydroxyl group in the constituent monomer of the contact lens or the hydroxyl group newly introduced by means of a plasma treatment and such.

"A Method of Introducing Phosphorylcholine Groups to the Hydroxyl Groups of a Contact lens"

A contact lens that contains 2-hydroxyethyl methacrylate and/or polyvinyl alcohol has hydroxyl groups. By reacting the chemical compound of formula (2) with these hydroxyl groups, phosphorylcholine groups can be introduced onto the contact lens surface by means of acetal bonding. This reaction can proceed easily under acidic conditions in water, in an organic solvent such as methanol, ethanol, dimethylformamide, dimethylsulfoxide, and tetrahydrofuran, or in a mixed solvent of water and the aforementioned organic solvent.

"Treatment Method 1"

A contact lens made of a HEMA (2-hydroxyethylmethacrylate polymer) can be treated by heating the chemical compound of formula (2) to a temperature ranging from room temperature to 100° C. in the presence of an acid catalyst such as hydrochloric acid, acetic acid, sulfuric acid, trifluoroacetic acid, and p-toluenesulfonic acid, using water or an organic solvent such as dimethylsulfoxide, dimethylformamide, and tetrahydrofuran as a medium. The introduction ratio can be controlled by adjusting the amount of the chemical compound of formula (2) to be added, the amount of the acid catalyst, and/or the reaction temperature.

"Treatment Method 2"

A contact lens made of a PVA (polyvinyl alcohol) can be treated by heating the chemical compound of formula (2) to a temperature ranging from room temperature to 100° C. in the presence of an acid catalyst such as hydrochloric acid, acetic acid, sulfuric acid, trifluoroacetic acid, and p-toluenesulfonic acid, using water or an organic solvent such as dimethylsulfoxide, dimethylformamide, and tetrahydrofuran as a medium. The introduction ratio can be controlled by adjusting the amount of the chemical compound of formula (2) to be added, the amount of the acid catalyst, and/or the reaction temperature.

The phosphorylcholine group of formula (1), introduced onto the contact lens surface by means of the method described above or the like, is, after a pre-treatment using perchloric acid, quantified with the molybdenum blue method for the quantitative analysis of phosphorus (Reference: 3.8.2 Phosphorus, Analysis, 4$^{th}$ edition, Experimental Chemistry Course (14), Maruzen).

The amount of the phosphorylcholine group of formula (1) introduced onto the contact lens is preferably 0.005 micromol/mg or more. If it is less than 0.005 micromol/mg then a sufficient protein adsorption suppression effect is not obtained sometimes; however, this does not apply to the case in which the phosphorylcholine group is introduced only on the contact lens surface. The protein adsorption suppression effect increases as the amount introduced increases; therefore there is no upper limit for the amount introduced.

EXAMPLES

Next, the present invention is described in detail by referring to Examples. The present invention is not limited to these Examples.

"Protein Adsorption Experiment"

The contact lenses of the present invention were prepared by using commercially available contact lenses. The protein adsorption suppression effect was compared based on the following evaluation method.

"Evaluation Method"

A contact lens was immersed in 3 ml of an artificial lacrimal fluid and left alone for 24 hours at 37° C. The protein level in the solution was quantified with the BCA method (the calibration curve: Albumin Bovine); the protein adsorption level was determined as the reduction in the proteins in the solution.

The artificial lacrimal fluid was obtained by dissolving the following ingredients in pure water: 1.20 mg/ml lysozyme, 3.88 mg/ml albumin, 1.61 mg/ml γ-globulin, 9.00 mg/ml sodium chloride, 0.14 mg potassium dihydrogen phosphate, and 0.80 mg/ml disodium hydrogen phosphate heptahydrate. (Reference) FDA Guideline Draft: Testing guidelines for class III soft(hydrophilic) contact lens solution, lens group compatibility test. Jul. 15, 1985.

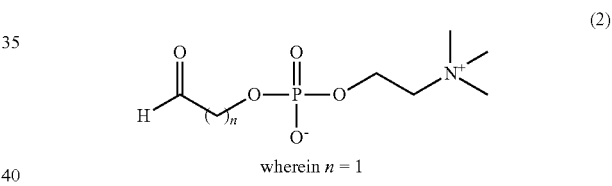

wherein $n = 1$

The aforementioned phosphorylcholine group-containing chemical compound is a prior art chemical compound obtained with the following Synthesis example 1.

Synthesis Example 1

An Aldehyde Chemical Compound Containing a Phosphorylcholine Group

1-α-glycerophosphorylcholine (450 mg) was dissolved in 15 ml of distilled water and cooled in an ice water bath. Sodium periodate (750 mg) was added, followed by five hours of stirring. The reaction fluid was concentrated under reduced pressure and dried under reduced pressure; methanol was then used to extract the target substance.

"The After-Treatment of a Contact Lens"

Polymacon (soft contact lens "Medalist" from Bausch & Lomb) and NelficonA (Focus Dailies from Ciba Vision) were used for the contact lenses, to which the chemical compound of formula (2) was covalently bonded by means of acetal bonding.

Example 1

One Polymacon was immersed in 2 ml of water, in which 10 mg of the phosphorylcholine-containing chemical compound of formula (2) was dissolved. 2 ml of 2N hydrochloric acid was then added and the concentration of the hydrochloric acid in the mixed solution was adjusted to 1M, followed by five hours of reaction at 70° C. The reaction fluid was cooled down to room temperature and rinsed thoroughly to obtain the target contact lens. The level of the introduced phosphorylcholine group of formula (1) was 0.0734 micromol/mg.

Example 2

One NelfilconA was immersed in 2 ml of water, in which 10 mg of the phosphorylcholine-containing chemical compound of formula (2) was dissolved. 2 ml of 2N hydrochloric acid was then added and the concentration of the hydrochloric acid in the mixed solution was adjusted to 1M, followed by five hours of reaction at 40° C. The reaction fluid was cooled down to room temperature and rinsed thoroughly to obtain the target contact lens. The level of the introduced phosphorylcholine group of formula (1) was 0.1688 micromol/mg.

"A method of Quantifying the Phosphorylcholine Group of Formula (1)"

The obtained contact lens was immersed in perchloric acid and heated up to 180° C. to be decomposed. The obtained solution was diluted with water, to which hexaammonium heptamolybdate tetrahydrate and L-ascorbic acid were added, followed by 5 minutes at 95° C. of color development time; the amount introduced was determined by means of the light absorption measurement at 710 nm. For the calibration curve, a sodium dihydrogen phosphate solution was used.

Comparative Examples 1-5

For comparison, the following commercially available contact lenses were used.

Comparative Example 1

EtafilconA (product name: 1-Day Acuvue from J & J)

Comparative Example 2

EtafilconA (product name: 1 Day Aquair from Ocular Science)

Comparative Example 3

NelfilconA (Focus Dailies from Ciba Vision)

Comparative Example 4

Polymacon (product name: Medalist from Bausch & Lomb)

Comparative Example 5

VifilconA (Focus from Ciba Vision)

Comparative Example 6

Based on the technique described in Patent Document 5, 10 mg of 1-α-glycerophosphorylcholine, 20 mg of 1,1-carbonyldiimidazole, and 20 mg of triethylamine were added to 3 ml of dimethylsulfoxide, followed by two hours of stirring at 50° C. NelfilconA, which was used in Example 2, was immersed in this solution, followed by 12 hours of reaction time at room temperature. The contact lens was thoroughly rinsed with dimethylsulfoxide and then with water; the phosphorus quantification showed the level of the introduced phosphorylcholine group to be at the detection limit, 0.0001 micromol/mg, or less, indicating that the reaction did not proceed.

Comparative Example 7

Based on the technique described in Patent Document 5, 10 mg of 1-α-glycerophosphorylcholine, 20 mg of 1,1-carbonyldiimidazole, and 20 mg of triethylamine were added to 3 ml of dimethylsulfoxide, followed by two hours of stirring at 50° C. NelfilconA, which was used in Example 2, was immersed in this solution, followed by 12 hours of reaction time at room temperature. The contact lens was thoroughly rinsed with dimethylsulfoxide and then with water; the phosphorus quantification showed the level of the introduced phosphorylcholine group to be at the detection limit, 0.0001 micromol/mg, or less, indicating that the reaction did not proceed.

FIG. 1 shows the results of protein adsorption for Examples 1-2 and Comparative examples 1-7. These results indicate that the contact lenses obtained by the preparation method of the present invention significantly suppress protein adsorption.

Next, the reaction treatment conditions for treating NelfilconA in Example 2 were changed and corresponding changes in the level of the introduced phosphorylcholine group were investigated.

The introduced levels of the phosphorylcholine group as functions of the reaction temperature, the acid catalyst level, and the amount of the chemical compound of formula (2) added are shown in Tables 1-3.

<The Effect of the Reaction Temperature>
The chemical compound of formula (2): 1 equivalent (for hydroxyl groups of the contact lens)
Acid Catalyst: 1M Hydrochloric Acid

TABLE 1

| Reaction temperature | Level of the introduced phosphorylcholine group |
| --- | --- |
| 70° C. | 0.5842 micromol/mg |
| 40° C. | 0.1688 micromol/mg |
| 25° C. | 0.0328 micromol/mg |

<The Effect of the Acid Catalyst Level>
The chemical compound of formula (2): 1 equivalent (for hydroxyl groups of the contact lens)
Reaction temperature 40 □

TABLE 2

| HCl concentration | Level of the introduced phosphorylcholine group |
| --- | --- |
| 1M | 0.1688 micromol/mg |
| 0.1M | 0.0149 micromol/mg |
| 0.01M | 0.0032 micromol/mg |

<The Effect of the Amount of the Chemical Compound of Formula (2) Added>
Acid Catalyst: 1M Hydrochloric Acid
Reaction temperature: 40 □

TABLE 3

| Amount of the chemical compound of formula (2) added | Level of the introduced phosphorylcholine group |
| --- | --- |
| 5 equivalents | 0.1688 micromol/mg |
| 3 equivalents | 0.1317 micromol/mg |
| 1 equivalent | 0.0447 micromol/mg |

As the results shown in Tables 1-3 indicate, the level of the introduced phosphorylcholine group can be easily controlled by changing the reaction treatment conditions. Preferable reaction treatment conditions are as follows.

Reaction temperature: Room temperature to 80° C., more preferably 40° C. 70° C.

Hydrochloric acid concentration: 0.01-5M, more preferably 0.1-1M

Level of the added phosphorylcholine chemical compound (2): 0.1-10 equivalents, more preferably 1-5 equivalents

INDUSTRIAL APPLICABILITY

The present invention can highly suppress protein adsorption on contact lenses and significantly prevent stains due to proteins.

The method of the present invention can be preferably used for soft contact lenses, for which protein staining is a fatal problem. It can be preferably used in particular for ionic soft contact lenses, which accelerate protein adsorption.

It can also be preferably used for hard contact lenses for extended wear and/or with oxygen permeability, to which proteins tend to be adsorbed.

The invention claimed is:

1. A method of manufacturing an eye lens material that prevents protein adsorption, said method comprising:

reacting in a reaction medium selected from the group consisting of water, an organic solvent, and a water/organic solvent mixture an eye lens material having OH groups with a phosphorylcholine group-containing compound of formula (1) below, thereby forming a compound having an acetal bond according to formula (2) below, to covalently bond the phosphorylcholine group-containing compound to the eye lens material:

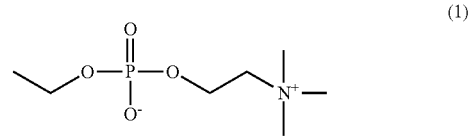

(1)

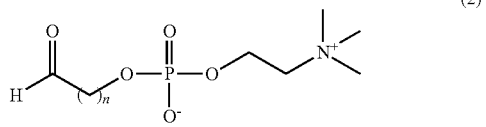

(2)

wherein $n$ denotes a natural number from 1-18.

2. The method of manufacturing the eye lens material that prevents protein adsorption of claim 1, wherein constituent monomers from which the eye lens material is formed comprise monomers containing an hydroxyl group.

3. The method of manufacturing the eye lens material that prevents protein adsorption of claim 1, wherein constituent monomers from which the eye lens material is formed comprise 2-hydroxyethylmethacrylate.

4. The method of manufacturing the eye lens material that prevents protein adsorption of claim 1, wherein the eye lens material is formed from constituent ingredients comprising polyvinyl alcohol.

5. A method of manufacturing an eye lens material which prevents protein adsorption wherein OH groups are first introduced onto the surface of the eye lens material by means of a plasma pretreatment, said method comprising reacting in a reaction medium selected from the group consisting of water, an organic solvent, and water/organic solvent mixture a plasma pretreated eye lens material having OH groups on the surface of the eye lens material with a phosphorylcholine group-containing compound of formula (1) below, thereby forming a compound having an acetal bond according to formula (2) below, to covalently bond the phosphorylcholine group-containing compound to the eye lens material:

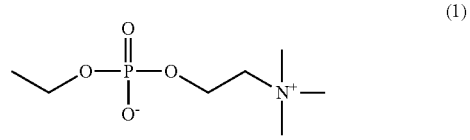

(1)

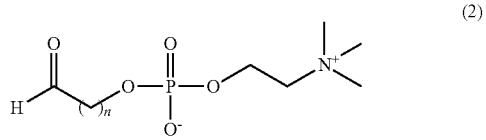

(2)

wherein $n$ denotes a natural number from 1-18.

6. A method for preventing protein adsorption on an eye lens material containing OH groups by means of an after-treatment, said method comprising:

reacting in a reaction medium selected from the group consisting of water, an organic solvent, and a water/organic solvent mixture said eye lens material having OH groups on the surface with a phosphorylcholine group-containing compound of formula (1) below, thereby forming an acetal bond according to formula (2) below, to covalently bond the phosphorylcholine group-containing compound to the eye lens material:

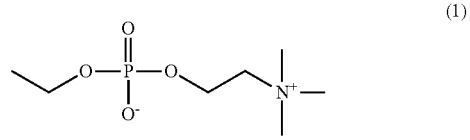

(1)

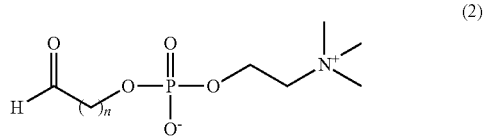

(2)

wherein $n$ denotes a natural number from 1-18.

* * * * *